(12) United States Patent
Ransome (10) Patent No.: US 9,907,912 B2
(45) Date of Patent: Mar. 6, 2018

(54) GELATIN BOWEL PREP WITH SYRINGE FOR COLONOSCOPY

(71) Applicant: John B. Ransome, Fairfield, CT (US)

(72) Inventor: John B. Ransome, Fairfield, CT (US)

( * ) Notice: Subject to any disclaimer, the term of this patent is extended or adjusted under 35 U.S.C. 154(b) by 58 days.

(21) Appl. No.: 14/867,374

(22) Filed: Sep. 28, 2015

(65) Prior Publication Data

US 2016/0089488 A1 Mar. 31, 2016

Related U.S. Application Data

(60) Provisional application No. 62/055,829, filed on Sep. 26, 2014.

(51) Int. Cl.
*A61M 5/315* (2006.01)
*A61M 5/31* (2006.01)

(52) U.S. Cl.
CPC ...... *A61M 5/3137* (2013.01); *A61M 5/31513* (2013.01); *A61M 2005/31516* (2013.01)

(58) Field of Classification Search
CPC .... A61M 5/31513; A61M 2005/31516; A61M 3/005; A61M 3/0262; A61M 5/3137; A61K 47/00
USPC ....................................................... 604/222
See application file for complete search history.

(56) References Cited

U.S. PATENT DOCUMENTS

| | | | |
|---|---|---|---|
| 3,424,158 A * | 1/1969 | Silver | A61D 7/00 604/218 |
| 5,328,711 A | 7/1994 | Coleman et al. | |
| 2004/0143005 A1* | 7/2004 | Barras | A61K 9/009 514/474 |
| 2012/0219642 A1* | 8/2012 | Nizam | A61K 31/195 424/724 |
| 2013/0006194 A1* | 1/2013 | Anderson | A61M 39/162 604/218 |
| 2015/0343096 A1* | 12/2015 | Takeda | A61K 49/0404 424/9.411 |
| 2016/0089499 A1* | 3/2016 | Okuda | A61M 5/31515 604/222 |

* cited by examiner

*Primary Examiner* — Jason Flick
(74) *Attorney, Agent, or Firm* — Ware, Fressola, Maguire & Barber LLP (57) ABSTRACT

A purgative product is provided which includes a gelatinous purgative and a dispenser for dispensing the gelatinous purgative. The dispenser includes a container with an open end and an opening on the opposite end. A plunger and sealing element can be inserted into the container, such that when the plunger is pushed towards the opening in the container, the gelatinous purgative between the sealing element and the opening of the container is pushed towards and out of the opening for ingestion by a user.

17 Claims, 9 Drawing Sheets

GELATIN BOWEL PREP WITH SYRINGE FOR COLONOSCOPY

CROSS-REFERENCE TO RELATED APPLICATIONS

The present application claims the benefit of U.S. Provisional Patent Application No. 62/055,829, filed on Sep. 26, 2014, which is hereby incorporated by reference in its entirety.

FIELD OF THE INVENTION

The present application relates to purgatives taken by patients prior to having a colonoscopy exam, surgical procedure or for cleansing one's colon, and in particular, a gelatin form purgative and syringe for administering the medication.

BACKGROUND OF THE INVENTION

Purgatives, or bowel preps as they are more commonly called, are very difficult to swallow. The purpose of bowel preps is to flush the patient's colon prior to exam by a physician. The biggest complaint patients have with colonoscopy exams is taking the bowel prep because of the horrible taste and amount of fluid ingested.

Colon cancer is the second leading cause of cancer death in the United States. It can easily be detected with today's technology, however a large portion of people who should be screened fail to get the exam. Part of the reason is the difficult preparation procedure. In order for a doctor to see the inner lining of the colon using a colonoscope, they need the patient to have a cleaned out colon. The current bowel preps on the market are used by either mixing a solution into a clear fluid drink or by taking multiple pills the night before the exam. A problem with these solutions is the unsavory taste of the solutions and the amount of fluid needed to flush the colon.

Directions seem to be another problem with the current products on the market. Patients get confused and have to call the doctor's office for advice. Some of the products require drinking a gallon of fluid the night before an exam. That is a lot of fluid considering it has an extremely salty taste and powdery texture. Some patients have to hold their noses when swallowing the contents. Patient compliance is low with these products due to the large amount of required fluid consumption.

The main problem with these preps being distasteful is that with each sip the medicine saturates one's whole mouth making them less inclined to follow the proper directions for use. Patients do not like the taste, so patients will not drink all the fluid. The patient also has to follow mixing instructions which for some can be confusing. This makes it harder for the doctor to see the patient's colon being that there is bio burden still left in the colon. There has not been a bowel prep developed that provides ease of use, quickness and a palatable taste in a manner that is pleasant to the patient.

SUMMARY OF THE INVENTION

According to the present invention, an improved bowel purgative and syringe is provided. The purgative is made of gelatin, pectin, polyethylene glycol-3350, sodium sulfate, magnesium citrate, potassium sulfate, bisacodyl, sweetener, coloring and other thickening agents. The purgative is contained in a translucent plastic oral syringe. In a preferred embodiment, the oral syringe is round in shape and eight ounces in size with a plunger shaft at one end. There are indents protruding on both sides of the round syringe where the user's thumbs are placed. The user can simply peel back a foil seal at the tip and place his or her thumbs on the indents while using the index fingers to push down on the shaft of a plunger. With the user's lips pressed against the smooth, oval tip, the shaft is compressed until all the gelatin slips into the user's mouth. Other possible ingredients include potassium sulfate, magnesium sulfate, sodium chloride, potassium chloride, sodium ascorbate, ascorbic acid and sodium picosulphate. The product can be made in a smaller version for pediatric medicines in gelatin form. The pre-filled syringes can come in different sizes or shapes depending on medical use.

Advantages of the invention include providing an improved bowel purgative, providing a quick and easy way for swallowing the medication with no mixing instructions and making the purgative more palatable tasting. Since the active ingredients are encapsulated in the gelatin, the user does not taste any medication. All the user tastes is the flavoring and it goes down quickly because of its semi-solid slippery state. This new product can also be sold over-the-counter with ingredients like polyethylene glycol and magnesium citrate for the colon cleansing market. There are a lot of health conscious people that do colon cleansing from time to time. The oral plastic syringe can be used for holding any medication in a gelatin or liquid form to be dispensed into ones mouth. It can be stored at room temperature but preferably is stored in a refrigerator to keep cold. The kit the oral syringes are stored in can also be vacuum sealed.

Further objects and advantages will become apparent from the following description and drawings.

DETAILED DESCRIPTION OF THE DRAWINGS

The present invention will now be described, with reference made to FIGS. 1A-5B.

The enclosed Figures show various views of the bowel prep dispenser or syringe 100 according to the invention. The syringe 100 includes a container 10, a sealing element such as a rubber seal 20 and a plunger 30. A purgative 200 can further be provided in the syringe 100, so that the syringe 100 with purgative 200 can be provided as an easily usable bowel prep product.

Figure 1A:
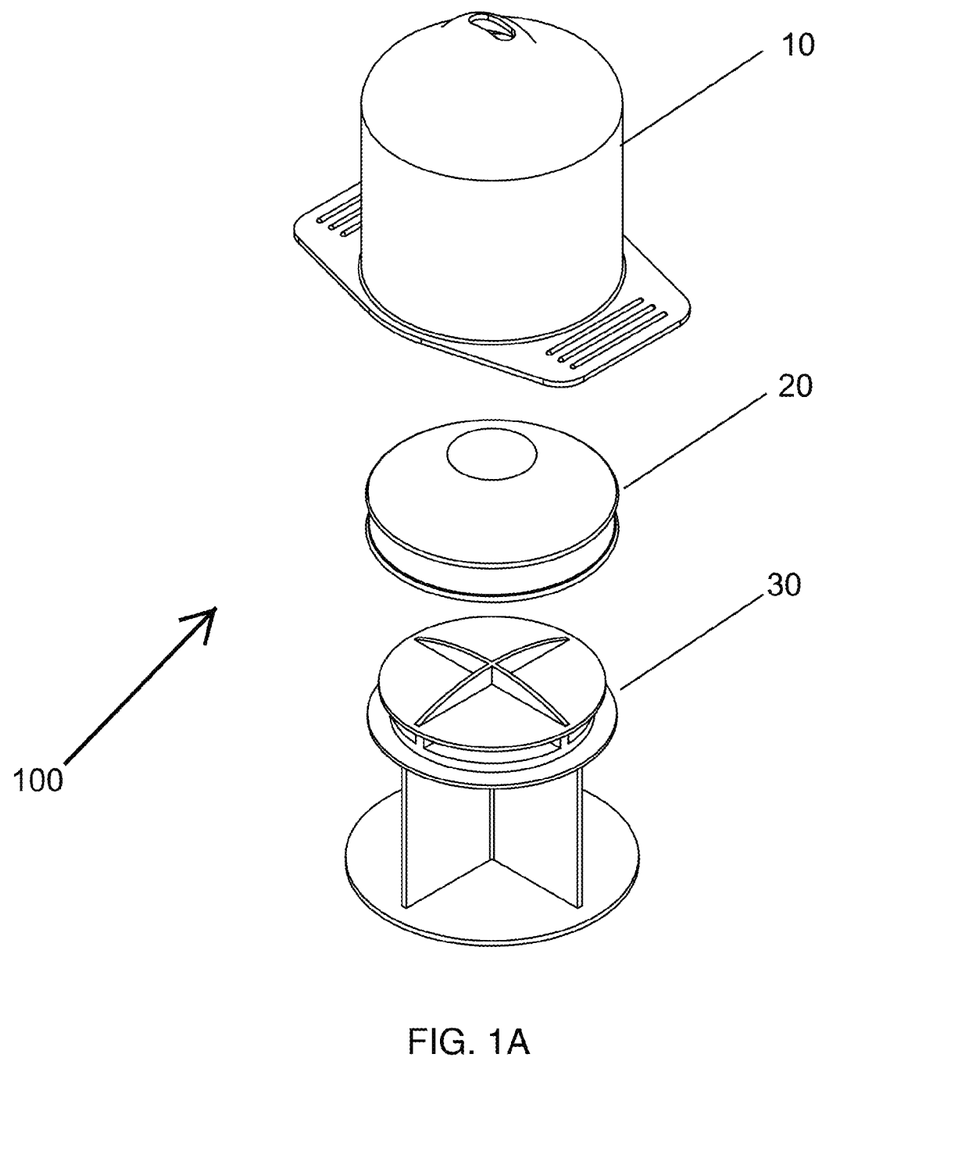
FIG. 1A shows an exploded view of the oral syringe according to an embodiment of the invention, including a cylinder, a plunger and a sealing element.
Figure 1B:
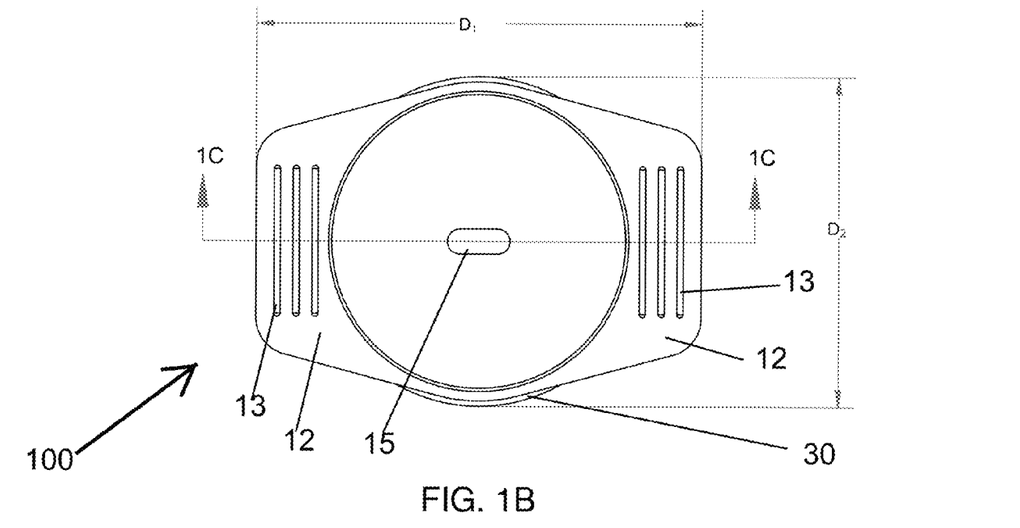
FIG. 1B shows an overhead view of the oral syringe according to an embodiment of the invention.
Figure 1C:
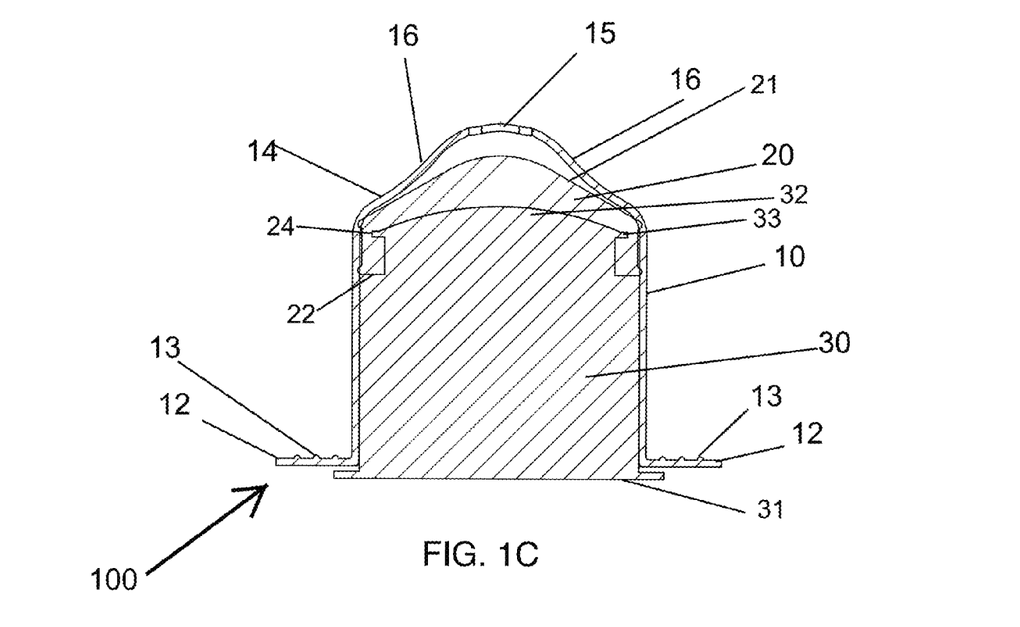
FIG. 1C shows a cross-sectional view of the oral syringe, according to an embodiment of the invention.
Figure 2A:
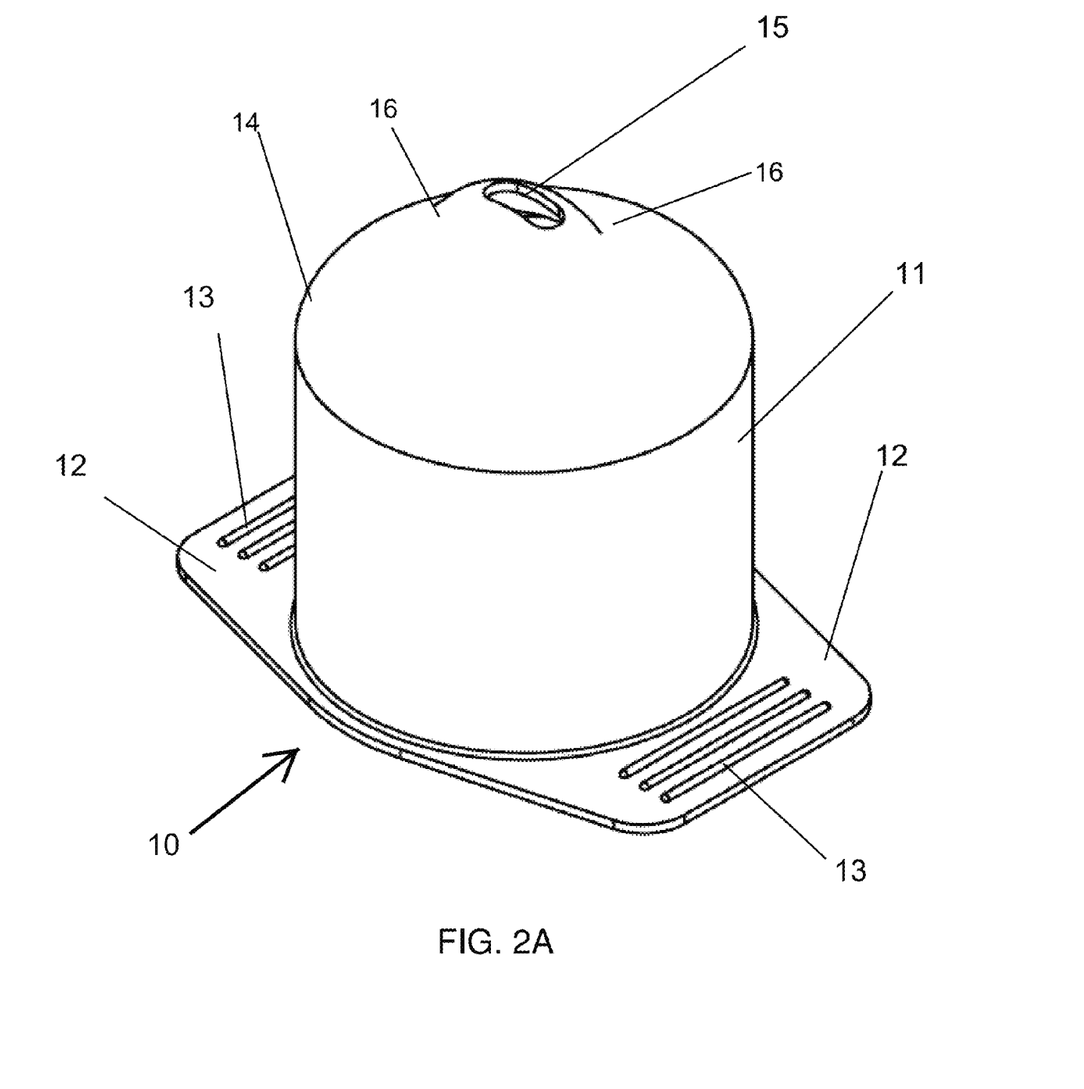
FIG. 2A shows a perspective view of the cylinder of the oral syringe, according to an embodiment of the invention.
Figure 2B:
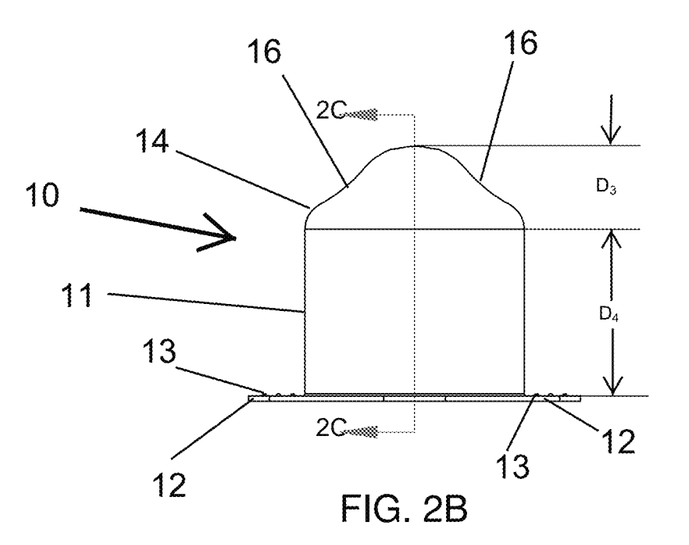
FIG. 2B shows a side view of the cylinder of the oral syringe, according to an embodiment of the invention.
Figure 2C:
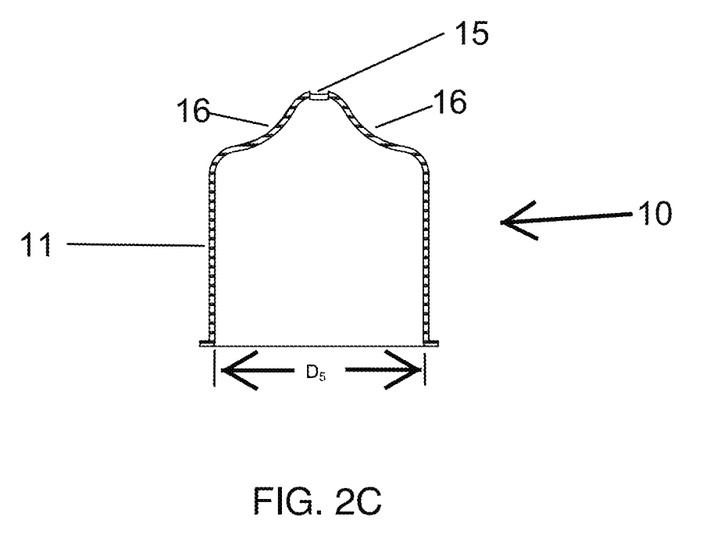
FIG. 2C shows a cross-sectional view of the cylinder of the oral syringe, according to an embodiment of the invention.

An exemplary embodiment of the container 10 of the syringe 100 is shown in FIGS. 2A-2C. In a preferred embodiment, the container 10 can be made of translucent plastic with the body consisting of a frosted look to give perception of coldness. The container 10 may be made from other materials in alternative embodiments. The container 10 includes a body section 11, which can be substantially cylindrical and hollow. At one end of the body 11, a pair of tabs 12 project out from the body 11, adjacent to an opening into the hollow body 11. The tabs 12 serve as a place where the user can place his or her thumbs to dispense the purgative 200 from the syringe 100. The tabs 12 may comprise grooves or indentations 13 to prevent thumbs from slipping off the tabs 12.

At the opposing end of the body 11, the cylindrical body 11 tapers to form a dispenser portion 14 of the container 10. The dispenser portion 14 of the container 10 includes an opening 15 at the tip of the container 10, through which the purgative 200 is dispensed. The dispenser portion 14 may also include grooves 16 adjacent to the opening 15, so that the user may press the opening 15 and tip of dispenser portion 14 against his or her mouth for ingesting the purgative 200.

During operation of the syringe 100, the purgative 200 is provided into the body 11 of the container 10 so that it can be dispensed through the opening 15. A plunger 30 is provided for use in forcing the purgative 200 out of the opening 15.

Figure 3A:
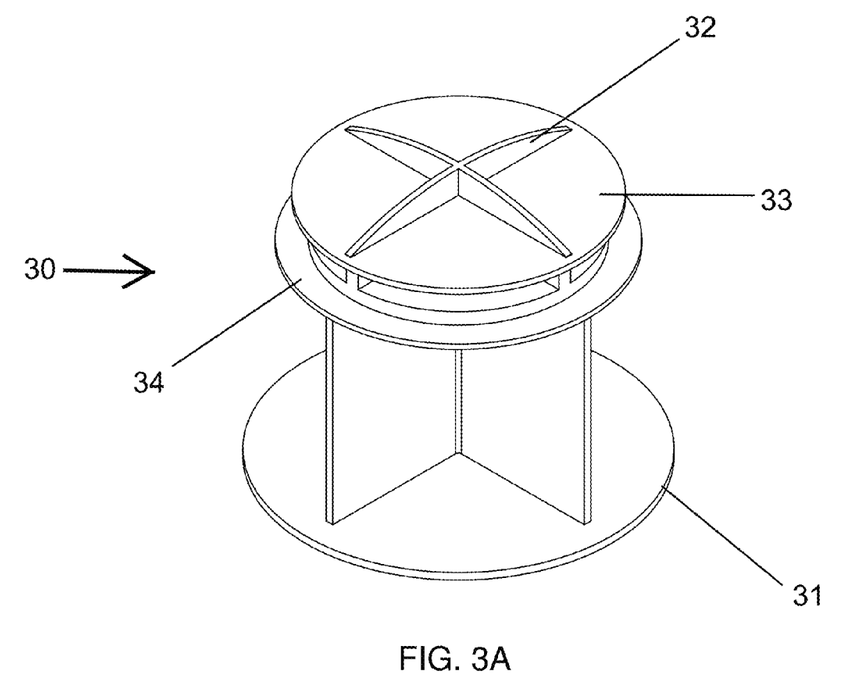
FIG. 3A shows a perspective view of the plunger of the oral syringe, according to an embodiment of the invention.
Figure 3B:
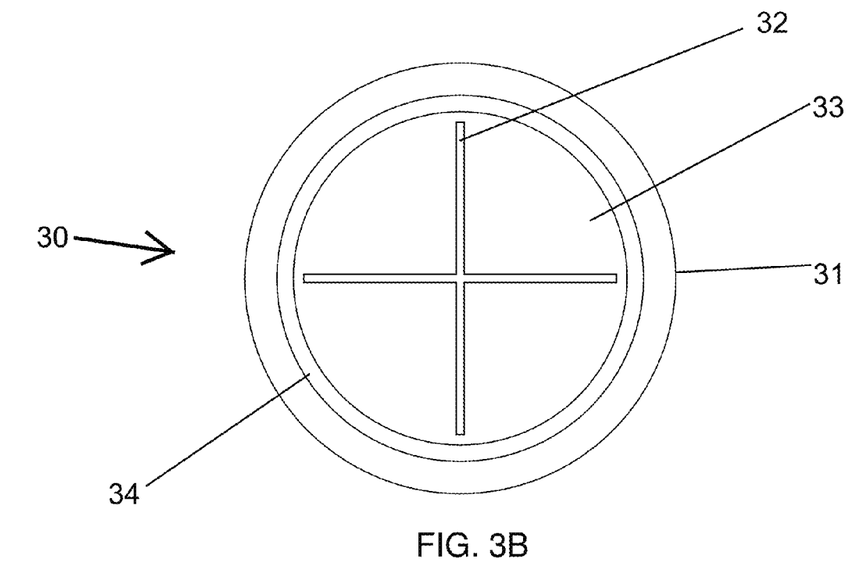
FIG. 3B shows an overhead view of the plunger of the oral syringe, according to an embodiment of the invention.
Figure 3C:
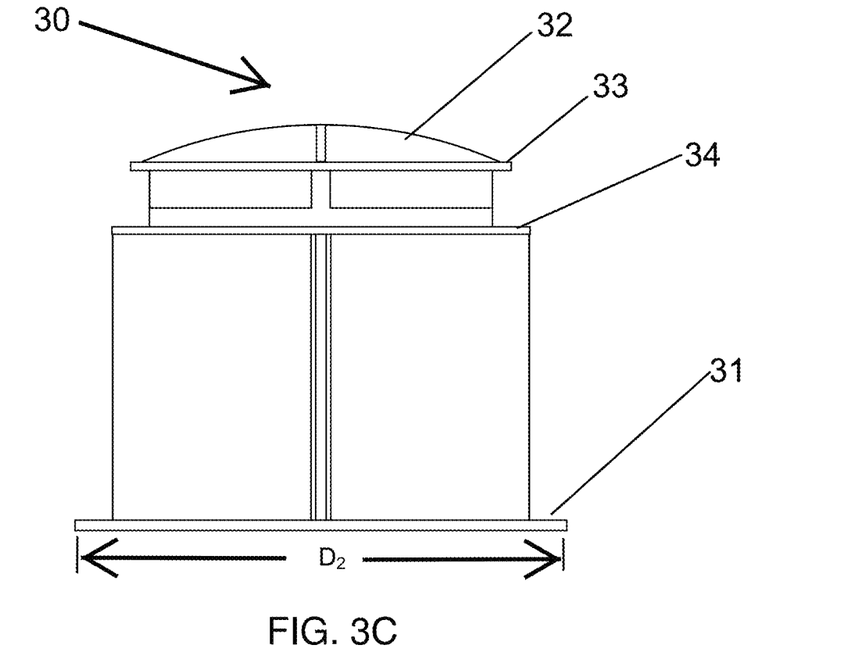
FIG. 3C shows a side view of the plunger of the oral syringe, according to an embodiment of the invention.

An exemplary embodiment of the plunger 30 is shown in FIGS. 3A-3C. The plunger 30 comprises a base 31. In the assembled syringe 100, the base 31 of the plunger 30 is positioned to be adjacent to the tabs 12 of the container 10 after the plunger has been depressed through the container 10. The base 31 of the plunger 30 may be circular, as shown in the Figures. The base 31 of the plunger 30 may have indentations (not shown) sides for receiving the user's index fingers to press down on the plunger 30, while the user's thumbs would be positioned on the grooves 13 of the tabs 12. The plunger 30 can be substantially cylindrical and dimensioned to be placed inside the hollow body 11 of the container 10.

Figure 4A:
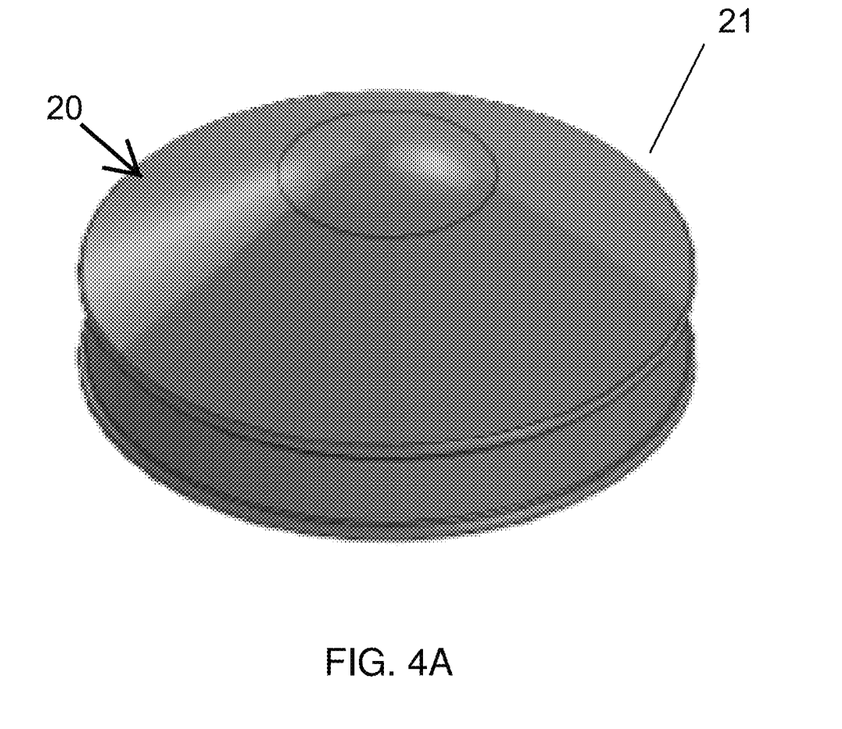
FIG. 4A shows a perspective view of the sealing element of the oral syringe according to an embodiment of the invention.
Figure 4B:
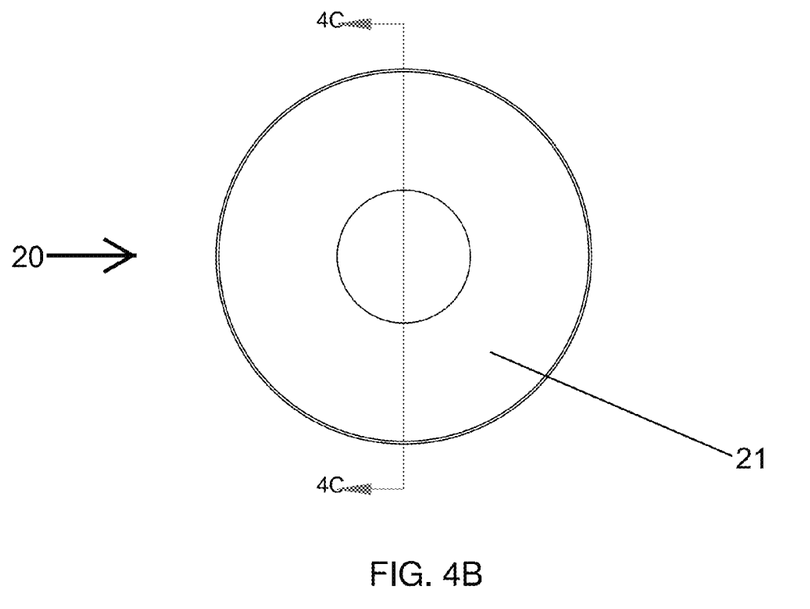
FIG. 4B shows an overhead view of the sealing element of the oral syringe according to an embodiment of the invention.
Figure 4C:
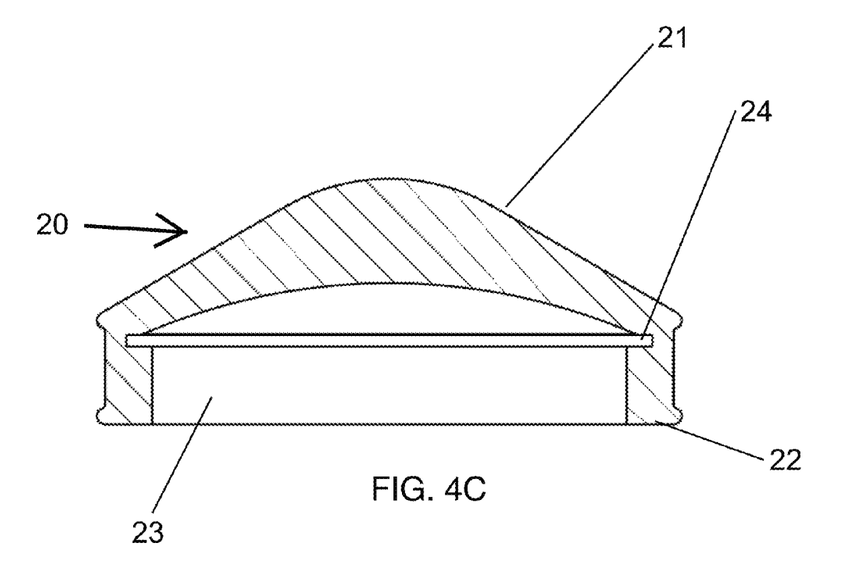
FIG. 4C shows a cross-sectional view of the sealing element of the oral syringe according to an embodiment of the invention.

The plunger 30 can be attached to a separate sealing element, such as a rubber seal 20 attached to the end of the plunger 30 opposite the base 31. An example of such a rubber seal 20 is shown in FIGS. 4A-4C. The rubber seal 20 creates a tight seal inside the container 10 when compressing purgative 200 out through the opening 15. The rubber seal 20 includes a top surface 21, which pushes the purgative 200 out of the opening 15. The top surface 21 may be sloped, as shown in FIGS. 4A-4C for example, in order to provide a better fit inside the dispensing section 14 of the container 10. In alternative embodiments, the sealing element may be made from a material other than rubber that is suitable for creating a seal inside the container 10 to keep the purgative 200 within the container 10 and force the purgative 200 towards the opening 15 when the plunger 30 is pushed.

The rubber seal 20 is configured to receive and attach to the plunger 30. The rubber seal 20 has a base 22 surrounding a cavity 23. The plunger 30 includes on its end opposite the base 31, one or more surface projections 32 projecting from an upper flange 33. Positioned a distance below the upper flange 33, a lower flange 34 is provided which has a greater diameter and circumference than the upper flange 33. The upper and lower flanges 33, 34 can be circular and extend outwardly from an invisible center line running through the center of the plunger 30. The cavity 23 of the rubber seal 20 is dimensioned for receiving the plunger 30. Within the cavity 23 of the rubber seal 20, a circumferential slot 24 is provided. The circumferential slot 24 is dimensioned to receive the upper flange 33 of the plunger 30, which attaches the rubber seal 20 to the plunger 30. Adjacent to the circumferential slot 24, a space is provided in the cavity 23 that is to receive the surface projections 32 of the plunger 30. When the plunger 30 is attached to the rubber seal 20, the lower flange 34 is oriented adjacent to the base 22 of the rubber seal 20. As a result of this arrangement, in the assembled syringe 100, the user can apply pressure on the base 31 of the plunger 30 towards the rubber seal 20 with index fingers, and in doing so the upper and/or lower flange 33, 34 will push the rubber seal 20 towards the opening 15, which will cause the top surface 21 of the rubber seal 20 to push the purgative 200 out of the opening 15.

It is noted that in alternative embodiments of the invention, the rubber seal 20 and plunger 30 can be configured differently from the manner shown in the Figures and described above. For example, it is envisioned that the surface projections 32 on the plunger 30 can be in forms other than the two intersecting projections 32, shown in the Figures, including for example a projecting sloped surface extending from the upper flange 33, similar to the shape of the top surface 21 of the rubber seal 20. The rubber seal 20 or other sealing element may also be attached to the plunger 30 by different means, including for example an adhesive. It is further envisioned that in certain embodiments, the plunger may be constructed with an integral sealing element secured to the plunger as a single and contiguous unit made from rubber, plastic or another suitable material.

A preferred embodiment of the purgative 200 according to the invention comprises a combination of ingredients, which can include gelatin, pectin, polyethylene glycol-3350, sodium sulfate, magnesium citrate, potassium sulfate, bisacodyl, sweetener (e.g., Splenda), coloring and other thickening agents. The purgative 200 is preferably in a gelatinous form for ingesting by a patient. The gelatinous form of the purgative 200 can be created using techniques known in the art for creating gelatinous, including for example, the method described in U.S. Pat. No. 5,328,711 for creating a gelatinous confection. In a preferred embodiment of the invention, the purgative 200 includes sweeteners or other ingredients which can improve the taste of the purgative for the patient. However, the purgative 200 also incorporates active ingredients so that the purgative 200 can perform its intended function of cleansing a patient's colon prior to an examination procedure. For example, for every eight ounces of purgative 200 provided in an oral syringe 100, the purgative 200 can include approximately seventeen grams of an active ingredient, such as sodium sulfate or magnesium citrate, or another active ingredient known in the art which can serve as a bowel purgative.

In an embodiment of the present invention, the assembly and use of the syringe 100 can begin by placing the purgative 200 into a container 10, such as the container 10 shown in FIGS. 2A-2C. In a preferred embodiment, the hollow container 10 is dimensioned to receive approximately eight ounces of the purgative 200. However, the present invention is not limited to such volume, and in alternative embodiments, containers can have different volumes, or different amounts of purgative 200 can be provided. The purgative 200 can be provided within the container 10 in one of two manners. According to one method, the opening 15 of the container 10 is sealed by a seal 17 and in the process of manufacturing the purgative 200, when the gelatin, purgative mixture is in a heated and substantially liquid form prior to cooling and solidifying, the appropriate amount of the mixture is poured into the container 10. The container 10 and liquid purgative 200 mixture is then cooled until the purgative 200 mixture substantially solidifies into the fully gelatinous form. According to a second method, the purgative 200 can be entirely manufactured into the fully gelatin form, and then the appropriate amount be placed into the container 10.

Figure 5A:
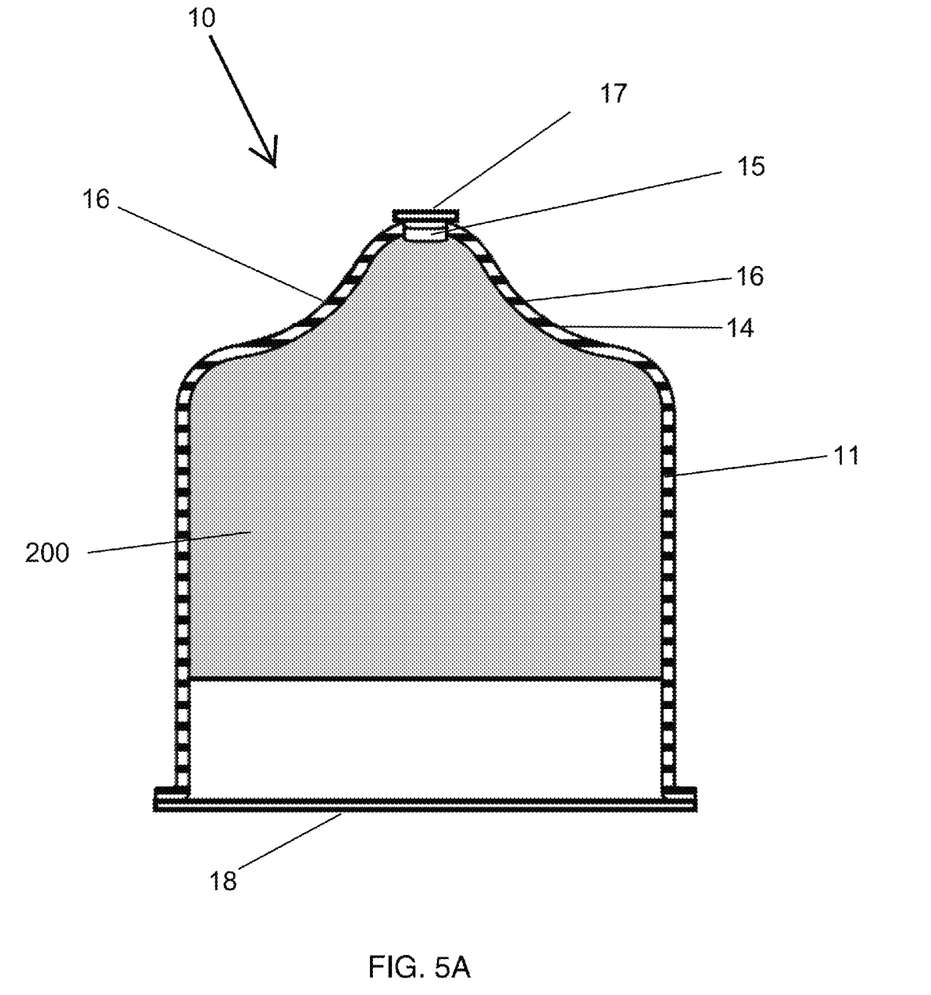
FIG. 5A shows a cross-sectional view of the cylinder of the oral syringe including a purgative according to an embodiment of the invention.

In accordance with an embodiment the invention, the syringe 100 including purgative 200 can be prepared for future use, meaning that the syringe 100 and purgative 200 are pre-packaged and can be obtained as a unitary product by a patient from a doctor or pharmacy, for example, for ingestion prior to a procedure. In such an embodiment, a sealing lid 17 can be provided, covering the opening 15 of the container 10 to preserve the purgative 200 and prevent the purgative 200 from inadvertently being dispensed. The sealing lid 17 can be, for example, a plastic or aluminum seal that is affixed to the container 10 and covers the opening 15, which can be peeled off by the patient prior to use. Additionally, in such an embodiment, a second sealing lid 18 can be provided which covers the base of the container 10, which can also be a plastic or aluminum seal that is affixed to the container 10 and covers the open base of the container 10, and which can be peeled off by the patient prior to use. An example of the container 10 filled with the purgative 200 and sealed by sealing lids 17 and 18 is shown in FIG. 5A.

The plunger 30 and rubber seal 20 are also provided during the assembly and use of the syringe 100. The plunger 30 and rubber seal 20 can be attached to each other in the manner described above, by securing the upper flange 33 of the plunger inside the circumferential slot 24 of the rubber seal 20. The attached plunger 30 and rubber seal 20 are inserted into the container 10 comprising the purgative 200. In certain embodiments, the plunger 30 and rubber seal 20 can be provided to the patient separately from the container 10 with purgative 200 (i.e., not inserted into the container 10), and the sealing lid 18 can be affixed to the base of container 10 and removed just prior to inserting the rubber seal 20 and plunger 30 into the container 10. In other embodiments, the entire syringe 100 with purgative 200 can be assembled and provided as a packaged unit, wherein the rubber seal 20 and plunger 30 are partially inserted into the container 10 so far as to not dispense the purgative 200 and the entire arrangement can be packaged. In such an embodiment, the rubber seal 20 can seal the purgative 200 rather than using a sealing lid 18.

It is further envisioned that according to another embodiment of the invention, the syringe 100 with purgative 200 can be prepared for immediate ingestion and use. In such an embodiment, a doctor, pharmacist or patient, for example, can fill the container 10 with the appropriate amount of purgative 200 (in liquid form followed by cooling or in solid form) and then insert the rubber seal 20 and plunger 30 as appropriate, without any sealing lids 17, 18 being provided.

Figure 5B:
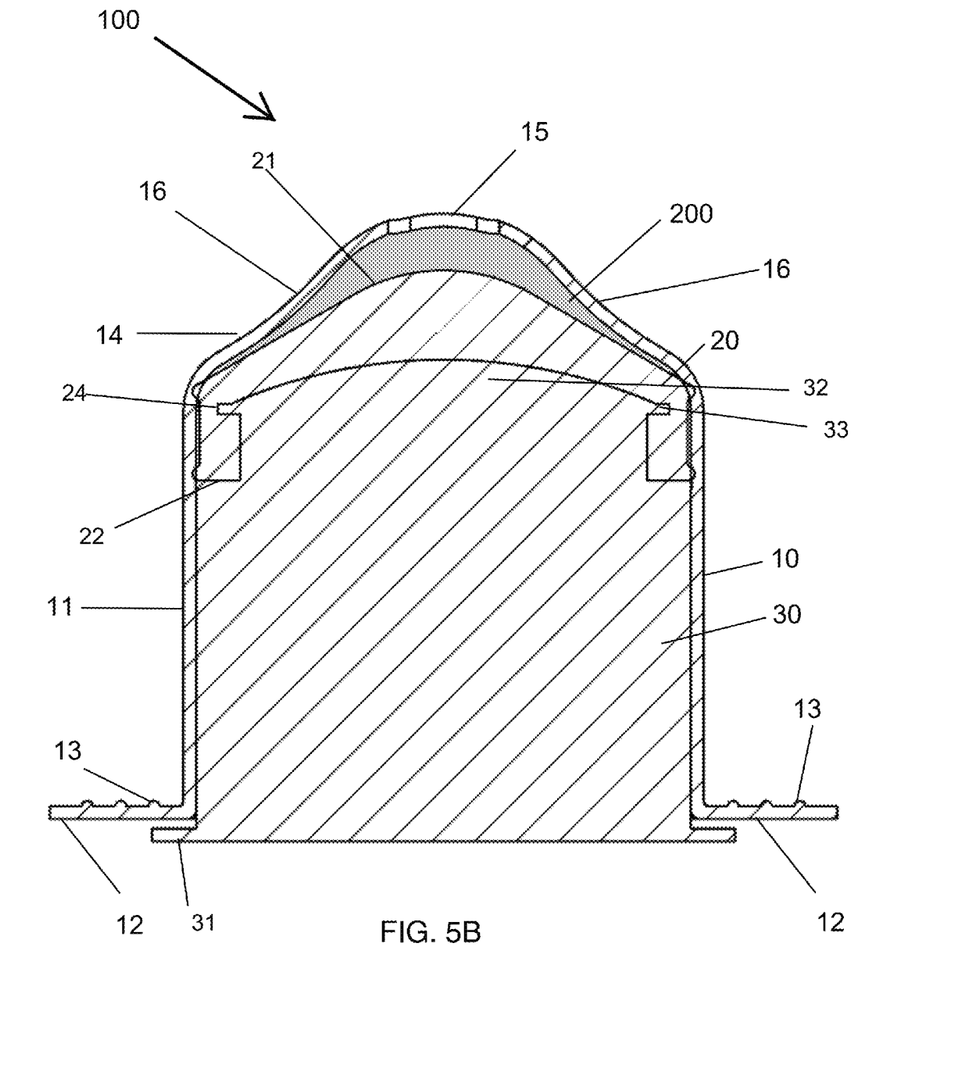
FIG. 5B shows a cross-sectional view of the oral syringe including a purgative, according to an embodiment of the invention.

In order to use the assembled bowel cleanser, the user can peel back either or both of the sealing lids 17, 18, if present, to fully expose the flavored and gelatinous purgative 200. If the rubber seal 20 and plunger 30 are not already inserted into the container 10, the user can insert the rubber seal 20 and plunger 30 into the container 10. The user then picks up the syringe 100, and can place their thumbs on the tabs 12 of the container 10 and push down on the base 31 of the plunger 30 with their index fingers, while holding their mouth against the dispensing portion 14 of the container until all of the purgative 200 is dispensed. An example of the syringe 100 with substantially all of the purgative 200 dispensed is shown in FIG. 5B.

In a preferred embodiment of the invention, various dimensions of the syringe 100 and its components can be as follows: The syringe 100 can have a length $D_1$ of approximately 4.42 inches and a width $D_2$ of approximately 3.275 inches. In the embodiments as shown in the Figures, the length $D_1$ of the syringe 100 corresponds to the length of the container 10 and the width $D_2$ corresponds to the diameter of the base 31 of the plunger 30. The dispensing portion 14 of the container 10 may have a height $D_3$ of approximately 1.125 inches and the body 11 of the container 10 may have a height $D_4$ of approximately 2.225 inches. The maximum inner diameter $D_5$ of the container 10 can be approximately 2.775 inches. The diameter of the upper flange 33 of the plunger 30 can be approximately 2.535 inches and the diameter of the lower flange 34 of the plunger 30 can be approximately 2.775 inches. The maximum diameter of the rubber seal 20 can be between approximately 2.775 inches and 2.825 inches.

The present invention is not limited to the exemplary dimensions shown in the Figures and described above, and is not limited to the shapes of the syringe 100 described herein, but these aspects of the invention can vary as appropriate, as would be understood by a person having ordinary skill in the art. For example, it is envisioned that the syringe 100 and its parts can be square, triangular or in the shape of any other polygon, extended into three-dimensions, and is not limited to the circular/cylindrical shape shown in the Figures.

While there have been shown and described and pointed out fundamental novel features of the invention as applied to preferred embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice.

What is claimed:
1. A purgative product comprising:
   a gelatinous, non-liquid bowel purgative for oral administration, and a dispenser for orally dispensing the gelatinous, non-liquid bowel purgative comprising:
   a container comprising a first open end and a second end comprising an opening;
   a plunger configured to be inserted into the first open end of the container; and
   a sealing element configured to be secured to a first end of the plunger and to be inserted into the first open end of the container;
wherein the gelatinous, non-liquid bowel purgative is stored inside the container in between the sealing element and the opening of the container and the dispenser is configured to dispense the gelatinous, non-liquid bowel purgative through the opening of the container by pushing a second end of the plunger towards the opening of the container; and
wherein the plunger and sealing element are a contiguous element made from the same material, such that the sealing element is not detachable from the plunger.

2. The purgative product according to claim 1, wherein the container further comprises a body section that tapers towards the opening on the second end of the container.

3. The purgative product according to claim 2, wherein the container further comprises a plurality of grooves on the second end of the container adjacent to the opening.

4. The purgative product according to claim 1, wherein the container further comprises a plurality of tabs projecting outwardly from the first end of the container.

5. The purgative product according to claim 4, wherein the plurality of tabs comprise grooves or indentations.

6. The purgative product according to claim 1, wherein the sealing element is made from rubber.

7. The purgative product according to claim 1, wherein the sealing element comprises:
   a cavity formed in a base of the sealing element configured to receive the plunger,
   a circumferential slot positioned inside the cavity, and
   a top surface configured to push the gelatinous, non-liquid bowel purgative towards the opening in the container when the plunger is pushed towards the opening in the container.

8. The purgative product according to claim 7, wherein the plunger comprises a first flange configured to be inserted into the circumferential slot inside the cavity of the sealing element to secure the plunger to the sealing element.

9. The purgative product according to claim 8, wherein the plunger further comprises a second flange configured to reside against the base of the sealing element secured to the plunger, and wherein pushing the second end of the plunger towards the opening of the container causes the second flange, the sealing element and gelatinous, non-liquid bowel purgative to be pushed towards the opening of the container.

10. The purgative product according to claim 8, wherein the plunger further comprises at least one projection projecting from the first flange and configured to reside against a surface in the cavity of the sealing element secured to the plunger, and wherein pushing the second end of the plunger towards the opening of the container causes the at least one projection, the sealing element and gelatinous, non-liquid bowel purgative to be pushed towards the opening of the container.

11. The purgative product according to claim 1, wherein the gelatinous, non-liquid bowel purgative includes at least one sweetening agent to improve the taste of the gelatinous, non-liquid bowel purgative and at least one active ingredient for colon cleansing.

12. The purgative product according to claim 11, wherein the at least one active ingredient is sodium sulfate or magnesium citrate.

13. The purgative product according to claim 11, wherein the gelatinous, non-liquid bowel purgative comprises approximately seventeen grams of the at least one active ingredient per eight ounces of gelatinous, non-liquid bowel purgative.

14. The purgative product according to claim 1, wherein the dispenser is dimensioned to store and dispense eight ounces of the gelatinous, non-liquid bowel purgative.

15. The purgative product according to claim 1, further comprising a removable plastic or aluminum seal covering the opening on the second end of the container, which is to be removed prior to dispensing the gelatinous, non-liquid bowel purgative through the opening.

16. The purgative product according to claim 1, further comprising a removable plastic or aluminum seal covering the first open end of the container, which is to be removed prior to inserting the sealing element and plunger into the first open end of the container.

17. A method for providing an orally administered purgative product comprising:
   providing a dispenser for orally dispensing a gelatinous, non-liquid bowel purgative, wherein providing a dispenser comprises:
      providing a container comprising a first open end and a second end comprising an opening;
      storing the gelatinous, non-liquid bowel purgative inside the container;
      securing a sealing element to a first end of a plunger; and
      inserting the sealing element and plunger into the first open end of the container so that the gelatinous, non-liquid bowel purgative is positioned in between the sealing element and the opening of the container;
   wherein the dispenser is configured to dispense the gelatinous, non-liquid bowel purgative through the opening of the container by pushing a second end of the plunger towards the opening of the container; and
   wherein the storing of the gelatinous, non-liquid bowel purgative inside the container comprises:
   creating a gelatin, purgative mixture that is in a substantially liquid state;
   sealing the opening of the container;
   pouring the gelatin, purgative mixture into the container; and
   cooling the gelatin, purgative mixture such that it forms the gelatinous, non-liquid bowel purgative in a non-liquid state.

* * * * *